United States Patent [19]
Goddard et al.

[11] Patent Number: 5,192,790
[45] Date of Patent: * Mar. 9, 1993

[54] 3-SUBSTITUTED-2-OXINDOLE DERIVATIVES AS INHIBITORS OF INTERLEUKIN-1 BIOSYNTHESIS

[75] Inventors: Carl J. Goddard, Groton; Douglas C. Hanson, Niantic; Gary R. Schulte, Stonington, all of Conn.

[73] Assignee: Pfizer Inc, New York, N.Y.

[*] Notice: The portion of the term of this patent subsequent to Aug. 29, 2006 has been disclaimed.

[21] Appl. No.: 808,491

[22] Filed: Dec. 17, 1991

Related U.S. Application Data

[63] Continuation of Ser. No. 529,050, May 25, 1990, which is a continuation-in-part of Ser. No. 421,445, Oct. 13, 1989, abandoned.

[51] Int. Cl.$^5$ ............................................. A61K 31/40
[52] U.S. Cl. ................................... 514/414; 514/863
[58] Field of Search ............................................ 516/414

[56] References Cited

U.S. PATENT DOCUMENTS

| | | | |
|---|---|---|---|
| 4,556,672 | 12/1985 | Kadin | 514/414 |
| 4,569,942 | 2/1986 | Kadin | 514/414 |
| 4,677,132 | 6/1987 | Hayward | 514/411 |
| 4,678,802 | 7/1987 | Kadin | 514/418 |
| 4,725,616 | 2/1988 | Kadin | 514/411 |
| 4,861,794 | 8/1989 | Otterness | 514/414 |
| 5,047,554 | 9/1991 | Ehrgott et al. | 548/486 |

FOREIGN PATENT DOCUMENTS

| | | |
|---|---|---|
| 8700432 | 1/1987 | PCT Int'l Appl. . |
| 8704618 | 8/1987 | PCT Int'l Appl. . |

OTHER PUBLICATIONS

Etienne, A., et al., Int. J. Tissue Reac. 7:459–462 (1985).
Murota, S. et al., Drugs Exptl. Clin. Res. 11:641-644 (1985).
Kragballe, K. et al., Arch Dermatol. 119:548-552 (1983).
Meghji, S. et al., Calcif. Tissue Int. 41 (Supplement 2):16 (1987).
Offenbacher, S. et al., J. Dent. Res. 67:244 (1988).
Fogh, K. et al., Arch. Dermatol. Res. 280:430–436 (1988).
Kunkel, S. L. et al., "Arachidonic Acid Metabolites Regulate Interleukin-1 Production", Biochemical and Biophysical Res. Comm. 128:892-897 (1985).
Smith, R. J. et al., "Human Neutrophil Activation with Interleukin-1", Biochemical Pharmacology 36:3851-3858 (1987).
Hayward, M. et al., "Mechanisms of bone loss: rheumatoid arthritis, periodontal disease and osteoporosis", Agents and Actions 22:251-254 (1987).
Hayward, M. et al., Annual Reports in Medicinal Chemistry 22, Sect. IV, Chapter 17, pp. 172-177 (1987).
Dinarello, C. A., "An Update on Human Interleukin-1: From Molecular Biology to Clinical Relevance", J. Clin. Immunol., 5:287-297 (1985).
Camp, R. D. et al., "Psoriatic Skin Lesions Contain Biologically Active Amounts of an Interleukin 1-Like Compound", J. Immunol., 137:3469-3474 (1986).
Dinarello, C. A., "Biology of Interleukin 1", FASEB J. 2, 108-115 (1988).
Dinarello, C. A. et al., "The Influence of Lipoxygenase Inhibitors on the In Vitro Production of Human Leukocytic Pyrogen and Lymphocyte Activating Factor (Interleukin-1)", Int. J. Immunopharmac., 6:43-50 (1984).
Dinarello, C. A. et al., "Role of Arachidonate Metabolism in the Immunoregulatory Function of Human Leukocytic Pyrogen/Lymphocyte-Activating Factor/Interleukin 1", J. Immunol., 130:890-895 (1983).
Meikle; M. C. et al., Chem. Abstracts 105:169829z.
McDonald, B. et al., "The Influence of a Novel Arachidonate Inhibitor, CP-66,248 on the Production and Activity of Human Monocyte IL-1", Arthritis Rheum. 32 (4 Suppl.):S17 (1988).
Otterness, I. G. et al., "Effects of CP-66,248 on IL-1 Synthesis of Murine Peritoneal Macrophages", Arthritis Rheum. 34 (4 Suppl.):S90 Abstract C55 (1988).

Primary Examiner—Leonard Schenkman
Attorney, Agent, or Firm—Peter C. Richardson; J. Trevor Lumb; Gregg C. Benson

[57] ABSTRACT

This invention relates to the use of certain 3-substituted-2-oxindole derivatives to inhibit interleukin-1 biosynthesis in a mammal. This invention also relates to the use of such compounds for treating interleukin-1 mediated disorders and dysfunctions such as bone and connective tissue metabolism disorders and immune dysfunction in a mammal. The methods of this invention comprise administering an interleukin-1 biosynthesis inhibiting amount of the compounds and salts of this invention to such a mammal.

41 Claims, No Drawings

3-SUBSTITUTED-2-OXINDOLE DERIVATIVES AS INHIBITORS OF INTERLEUKIN-1 BIOSYNTHESIS

CROSS REFERENCE TO RELATED APPLICATION

This application is a continuation of copending application Ser. No. 07/529,050, filed May 25, 1990, which is a continuation-in-part of copending application Ser. No. 07/421,445, filed Oct. 13, 1989, now abandoned.

BACKGROUND OF THE INVENTION

1. Field of the Invention

This invention relates to the use of certain 3-substituted-2-oxindole derivatives and the pharmaceutically-acceptable base salts thereof to inhibit interleukin-1 biosynthesis in a mammal. This invention also relates to the use of such compounds for treating interleukin-1 mediated disorders and dysfunctions such as bone and connective tissue metabolism disorders and immune dysfunction in a mammal. The methods of this invention comprise administering an effective amount of the compounds and salts of this invention to such a mammal.

2. General Background

Certain 3-substituted-2-oxindole-1-carboxamides of the formula

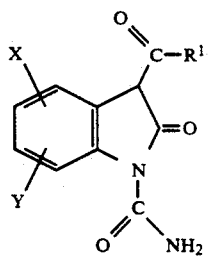

and the pharmaceutically-acceptable base salts thereof wherein, inter alia, X and Y are each H, F, Cl, Br or $CF_3$; and $R^1$ is —$(CH_2)_2$—Q—$R°$ where n is zero, Q is a divalent radical derived from a compound selected from the group consisting of, inter alia, furan, thiophene, thiazole, oxazole and isoxazole and $R°$ is H or $(C_1-C_3)$-alkyl are disclosed in U.S. Pat. No. 4,556,672 which is assigned to the assignee hereof. That patent discloses that those compounds, in addition to being useful as antiinflammatory and analgesic agents, are inhibitors of both the cyclooxygenase (CO) and lipoxygenase (LO) enzymes. The teachings thereof are incorporated herein by reference.

Certain 3-substituted-2-oxindole derivatives of the formula

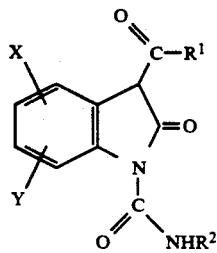

and the pharmaceutically-acceptable base salts thereof wherein, inter alia, X and Y are each H, F, Cl, Br or $CF_3$; and $R^1$ is —$(CH_2)_n$—Q—$R°$ where n is zero, Q is a divalent radical derived from furan, thiophene, thiazole, oxazole or isoxazole and $R°$ is H or $(C_1-C_3)$alkyl; and $R^2$ is $(C_1-C_6)$alkyl are disclosed in U.S. Pat. No. 4,569,942 which is assigned to the assignee hereof. That patent discloses that those compounds, in addition to being useful as antiinflammatory and analgesic agents, are inhibitors of both the cyclooxygenase (CO) and lipoxygenase (LO) enzymes. The teachings thereof are incorporated herein by reference.

U.S. patent applications Ser. No. 340,113, filed Apr. 18, 1989 and Ser. No. 473,266, filed Jan. 31, 1990, both of which are assigned to the assignee hereof, disclose certain 3-substituted-2-oxindole compounds of the formula

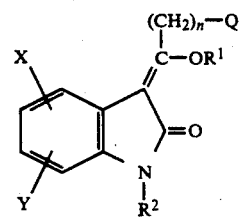

and the pharmaceutically-acceptable base salts thereof wherein, inter alia, X and Y are each H, F, Cl, Br or $CF_3$; $R^1$ is H; $R^2$ is $CONR^7R^8$ wherein $R^7$ is H and $R^8$ is H or $(C_1-C_6)$alkyl; Q is

where $Q^1$ is

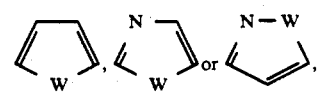

W is O or S, A and B are various substituents provided A and B cannot both be H nor A be H and B be $(C_1-C_4)$alkyl; and the tautomeric form thereof as a ketone. That application discloses that those compounds are useful as inhibitors of prostaglandin $H_2$ synthase and interleukin-1 biosynthesis, per se, and as analgesic, antiinflammatory and antiarthritic agents in the treatment of chronic antiinflammatory diseases.

U.S. Pat. No. 4,861,794, assigned to the assignee hereof, discloses the use of compounds of the formula

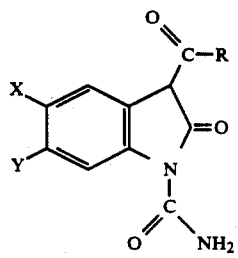

and the pharmaceutically-acceptable base salts thereof wherein X is H, Cl or F; Y is H or Cl; and R is benzyl or thienyl to inhibit biosynthesis of interleukin-1 (IL-1) and to treat IL-1 mediated disorders and dysfunctions.

Interleukin-1 (IL-1) has been reported to stimulate bone resorption both in vitro and in vivo. Hayward, M. and Fiedler-Nagy, Ch., Agents and Actions, 22, 251–254 (1987). It is also reported therein that IL-1, inter alia, induces the production of prostaglandin $E_2$ ($PGE_2$). $PGE_2$ is a stimulator of bone resorption and has been implicated in bone loss. Hayward, M. A. and Caggiano, T. J., Annual Reports in Medicinal Chemistry, 22, Sect. IV, Chapter 17, 172–177 (1987). Osteoporosis is defined as a debilitory loss of bone mineral which results in higher fracture rates. See Hayward, M. A. and Caggiano, T. J., supra, and references cited therein.

Interleukin-1 has been reported to be involved in the pathogenesis of many diseases. See Dinarello, C. A., J. Clin. Immunol., 5, 287–297 (1985), the teachings of which are incorporated herein by reference. Further still, elevated levels of IL-1 like material have been found to be associated with psoriasis. Camp, R. D., et al., J. Immunol., 137, 3469–3474 (1986).

The non-steroidal antiinflammatory agent etodolac, 1,8-diethyl-1,3,4,9-tetrahydropyrano[3,4-b]-indole-1-acetic acid, has been disclosed in U.S. Pat. No. 4,677,132 to lower $PGE_2$ and reduce bone resorption. Etodolac has the formula

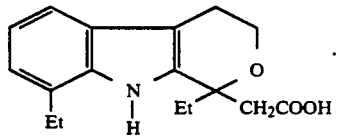

It has been reported that therapeutic levels of nonsteroidal antiinflammatory agents such as indomethacin and ibuprofen do not reduce IL-1 production. Similarly, cyclosporine A had no such effect. Corticosteroids, however, are effective in reducing IL-1 production. Dinarello, C. A., supra. Certain lipoxygenase inhibitors such as 5,8,11,14-eicosatetraynoic acid (ETYA) and 3-amino-1,3-trifluoromethylphenyl-2-pyrazoline (BW755C) have been reported to decrease in vitro production of leukocytic pyrogen (putative IL-1) from human monocytes. Dinarello, C. A., et al., Int. J. Immunopharmac., 6, 43–50 (1984).

However, until the invention herein, there was no report of use or intent to use the compounds or salts of this invention to inhibit IL-1 biosynthesis independent of lipoxygenase inhibition and to treat IL-1 mediated disorders and dysfunctions such as certain bone and connective tissue metabolism disorders and certain immune dysfunctions with such compounds nor any appreciation of their role in such treatments.

SUMMARY OF THE INVENTION

This invention relates to the use of certain 3-substituted-2-oxindole derivatives of the formula

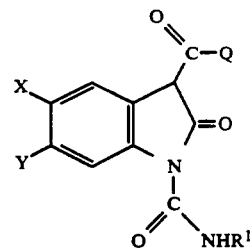

and the pharmaceutically-acceptable base salts thereof wherein X and Y are each H, F, Cl, Br or $CF_3$; $R^1$ is H or ($C_1$–$C_4$)straight or branched-chain alkyl; and Q is

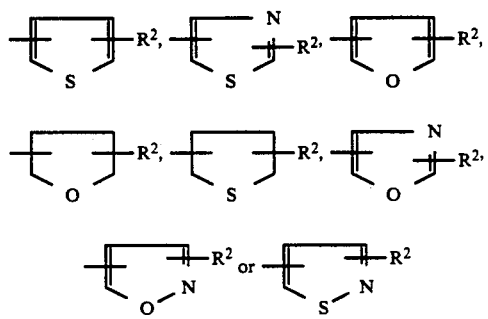

where $R^2$ is H or ($C_1$–$C_3$)alkyl, provided that when Q is

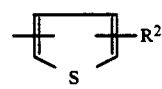

and $R^2$ is H, $R^1$ is not H, to inhibit the biosynthesis of IL-1, which inhibition is independent of their lipoxygenase inhibiting activity, and thus are useful in treating IL-1 mediated disorders and dysfunctions such as certain disorders of bone and connective tissue metabolism and dysfunctions of the autoimmune system in mammals. Such bone metabolism disorders include, but are not limited to osteoporosis. By way of example and not of limitation, such connective tissue metabolism disorders include periodontal disease and tissue scarring. Further, examples of IL-1 mediated immune dysfunctions include, but are not limited to, allergy and psoriasis.

While the compounds of formula I, above, are shown as a ketone, it is to be understood that the compounds of formula I can, under appropriate conditions, assume one or more tautomeric forms such as, for example:

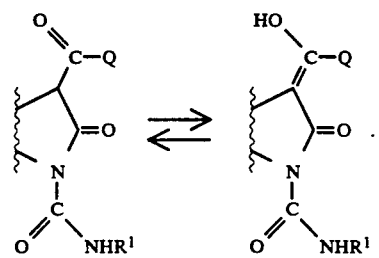

All tautomeric forms of the compounds of formula I are within the scope of this invention and the appendant claims, and are deemed to be depicted by formula I.

The methods of using the compounds and their pharmaceutically-acceptable base salts comprise administering to a mammal an effective amount of such compounds. Administration can comprise any known method for therapeutically providing a compound to a mammal such as by oral or parenteral administration as defined hereinbelow.

DETAILED DESCRIPTION OF THE INVENTION

The compounds of this invention which are of the Formula I, above, wherein $R^1$ is H and the preparation thereof are disclosed in U.S. Pat. No. 4,556,672, the teachings of which are incorporated herein by reference. The compounds of this invention which are of the Formula I, above, wherein $R^1$ is $(C_1-C_4)$straight or branched-chain alkyl and the preparation thereof are disclosed in U.S. Pat. No. 4,569,942, the teachings of which are incorporated herein by reference. This invention concerns new uses for compounds of Formula I, above, which comprise methods for inhibiting interleukin-1 (IL-1) biosynthesis in a mammal independent of inhibition of lipoxygenase. Also within the scope of this invention are methods of treating interleukin-1 mediated disorders and dysfunctions such as bone and connective tissue metabolism disorders and immune dysfunction.

Of the methods described above, preferred therein are those where the compound employed is of the Formula I, above, wherein $R^1$ is H or t-butyl; those wherein in said compound Q is

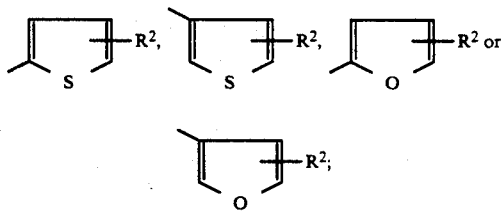

those wherein in said compound Q is

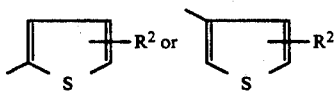

and $R^2$ is $CH_3$; those wherein in said compound Q is

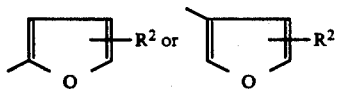

and $R^2$ is H or $CH_3$; those wherein in said compound Q is

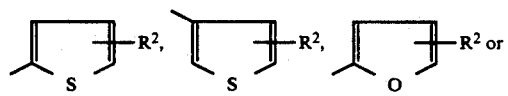

-continued

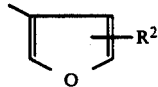

where $R^2$ is H and $R^1$ is ethyl or t-butyl; and those wherein in said compound X is Cl and Y is H.

As disclosed in U.S. Pat. No. 4,556,672 and U.S. Pat. No. 4,569,942, the compounds of this invention hereinabove described are acidic and form base salts. All such base salts are within the scope of this invention and can be formed as taught by that patent. Such suitable salts, within the scope of this invention, include both the organic and inorganic types and include, but are not limited to, the salts formed with ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of bases which form such base salts include ammonia, primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred are the sodium salts.

Also within the scope of this invention are the solvates such as the hemihydrates and monohydrates of the compounds hereinabove described.

Interleukin-1 is known by those skilled in the art to exist in at least two forms which are referred to as the $\alpha$ and $\beta$ forms. Dinarello, C. A., FASEB J., 2, 108–115 (1988). As used throughout this specification and the appendant claims, the term interleukin-1 (IL-1) refers to all such forms of IL-1 including IL-1$\alpha$, IL-1$\beta$ and IL-1$\alpha$ and IL-1$\beta$ collectively.

The methods of this invention comprise administering the invention compounds and the pharmaceutically-acceptable base salts thereof to a mammal. Such compounds and their salts can be administered to said mammal either alone or, preferably, in combination with pharmaceutically-acceptable carriers or diluents in a pharmaceutical composition, according to standard pharmaceutical practice. Such administration can be oral or parenteral. Parenteral administration as used herein includes, but is not limited to, intravenous, intramuscular, intraperitoneal, subcutaneous, transdermal and topical including, but not limited to oral lavage, administration. However, it is generally preferred to administer such compounds and their salts orally.

In general, these compounds and their salts are most desirably administered in doses ranging from about 0.5 mg/kg up to about 4 mg/kg per day for oral administration and from about 0.01 mg/kg up to about 4 mg/kg per day for parenteral administration, although variations will still necessarily occur depending upon the weight of the subject being treated. The appropriate dose for inhibiting IL-1 biosynthesis in a mammal and for treatment of IL-1 mediated bone metabolism disorder, IL-1 mediated connective tissue metabolism disorder or IL-1 mediated immune dysfunction with the compounds and their salts of this invention will be readily determined by those skilled in the art of prescribing and/or administering such compounds. Nevertheless, it is still to be appreciated that other variations may also occur in this respect, depending upon the species of mammal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur, provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the preferred mode of administration of the compounds of this invention or their pharma-ceutically-acceptable base salts is oral, they may be administered parenterally as well.

For purposes of parenteral administration, solutions of these particular compounds in sesame or peanut oil or in aqueous propylene glycol may be employed, as well as sterile aqueous solutions of the corresponding water soluble base salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. Needless to say, the necessary steps should be taken throughout the preparation of these injectable solutions to insure that the final products are obtained in a sterile condition. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in European Patent Application Publication No. 217983 and in European Patent Application Publication No. 331382, both of which are assigned to the assignee of this invention, and the teachings of which are incorporated herein by reference. For purposes of topical administration, the dosage form of the particular compound may include, by way of example and not of limitation, solutions, lotions, ointments, creams and gels.

The ability of the compounds of formula I to inhibit interleukin-1 biosynthesis is demonstrated by the assay procedure described below.

C3H/HeN mice (Charles River, Wilmington, Mass.) are sacrificed by cervical dislocation and their abdomens sprayed with 70% ethanol to prevent bacterial contamination of the subsequent cellular preparation. Into the peritoneum of each mouse is injected 8 ml of RPMI[1] containing 5% FCS[2], penicillin-streptomycin (100 units/ml–100 μg/ml) and glutami (2 mM). The peritoneum is kneaded to help free cells. Then, an incision through the skin of the abdomen is made to expose the underlying muscle layer. The peritoneal fluid is removed with a 20 gauge needle by inserting the needle, bevel down, through the exposed muscle layer just below the sternum. The peritoneal fluid from six mice is pooled in a plastic conical tube and microscopically examined for bacterial contamination. Uncontaminated fluid is centrifuged at about 600xg for six minutes and the supernatant decanted. The pelleted cells from five to six tubes are combined and resuspended in a total of 20 ml of RPMI-FCS[3]. The cell number is then ascertained using a hemacytometer and cell viability determined with Trypan Blue staining also using a hemacytometer. The cells are then diluted to $3 \times 10^6$ cells/ml using RPMI-FCS. To the wells of a 35 mm well plate is added 1 ml of the above cell suspension. The cells are incubated for 2 hours at 37° C. in a 5% $CO_2$ atmosphere to cause adherence of the macrophages to the walls of the wells. The supernatant is removed by swirling the wells vigorously and decanting. The adherent cells (i.e., macrophages) are washed twice with RPMI-SP[4]. To the wells containing adherent cells is added 1 ml of the compound under study at concentrations ranging from 0.1 to 100 μg/ml in RPMI containing 1% FCS or 1 ml of RPMI containing 1% FCS as a control. Then, 100 μl of LPS[5] in RMI containing 1% FCS (1 mg/5 ml) is added to each well. The plates are incubated at 37° C. in a 5% $CO_2$ atmosphere for 24 hours. The supernatants are removed and either assayed for IL-1 immediately or otherwise refrigerated or frozen

[1]RPMI-1640 medium (Hazelton Research Products, Inc., Lenexa, Kans.)
[2]Fetal calf serum which has been screened for good responsiveness to IL-1 in which the thymocyte assay (Hyclone Laboratories, Logan, Utah) and for low spontaneous proliferation in the absence of IL-1.
[3]RPMI-1640 medium containing 5% fetal calf serum.
[4]RPMI containing penicillin-streptomycin (100 units/ml-100 μg/ml) and glutamine (2 mM).

[5]Refined purified lipopolysaccaride from *Salmonella minnesota* which has been checked to determined that the C3H/HeJ mouse is unresponsive thereto.

The supernatants are assayed quantitatively for IL-1 according to the receptor binding assay described below. A standard curve is generated as follows. EL4-6.1 murine thymoma cells [10–15×10$^6$ cells/ml in binding buffer (RPMI 1640, 5% FCS, 25 mM HEPES, 0.01% NaN$_3$, pH 7.3)] are added to varying amounts of unlabeled murine rIL-1α [recombinant IL-1α produced in *Escherichia coli* from the published sequence of amino acids 115-270 for IL-1α, Lomedico, P. M., et al., Nature, 312 458–462 (1984)](40 pg/ml to 40 ng/ml) and incubated for 1 hour at 4° C. with continuous shaking, after which 0.5 ng/ml of human $^{125}$I-rIL-1α (New England Nuclear, Boston, Mass.) is added and shaking continued for an additional 4.5 hours. Total assay volume is generally 0.5 ml. Samples are filtered with a Yeda apparatus (Linca Co., Tel-Aviv, Israel) through Whatman GF/C2.4 cm glass fiber filters (blocked with 0.5% powdered milk for 2 hours at 37° C.) and washed once with 3 ml of ice-cold buffer. Filters are counted in a Searle gamma counter and non-specific binding is taken as the cpm bound in the presence of 200 ng/ml unlabeled rIL-1α. A Hill calibration curve is constructed by plotting log (Y/100-Y) vs. log C where Y represents the percent of control $^{125}$I-rIl-1α binding and C is the concentration of unlabeled rIL-1α. A linear least-squares line is fitted through Y values between 20 to 80%. Then, to quantitate IL-1 levels in the supernatants obtained as described above, diluted supernatants replace rIL-1α in the above protocol and measured percent binding values are used to determine IL-1 concentrations from a standard Hill plot. Each dilution is assayed in duplicate and generally only dilutions with Y values between 20 to 80% are used to calculate average IL-1 levels.

At concentrations relevant to use of the compounds herein, it has been found that the compounds of this invention do not inhibit lipoxygenase when tested in vitro in the presence of serum.

What is claimed is:

1. A method of inhibiting interleukin-1 biosynthesis in a mammal in need thereof which comprises administering to said mammal an interleukin-1 biosynthesis inhibiting amount of a compound of the formula

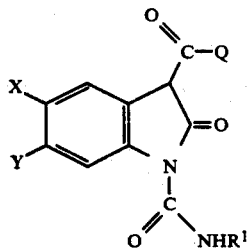

or a pharmaceutically-acceptable base salt thereof, wherein X and Y are each H, F, Cl, Br or CF$_3$; R$^1$ is H or (C$_1$–C$_4$) straight or branched-chain alkyl; and Q is

where R$^2$ is H or (C$_1$–C$_3$)alkyl that when R$^2$ is H, R$^1$ is not H.

2. The method according to claim 1 wherein Q is

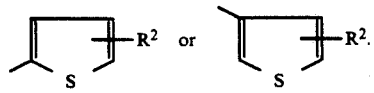

3. The method according to claim 1 wherein R$^1$ is ethyl or t-butyl.
4. The method according to claim 1 wherein R$^1$ is H.
5. The method according to claim 2 wherein X is Cl; Y is H; R$^1$ is H, ethyl or t-butyl; and R$^2$ is H or CH$_3$.
6. The method according to claim 2 wherein X is Cl; Y is H; R$^1$ is H; and R$^2$ is CH$_3$.
7. The method according to claim 1 wherein the compound or a pharmaceutically-acceptable base salt thereof is administered orally.
8. The method according to claim 1 wherein the compound or a pharmaceutically-acceptable base salt thereof is administered parenterally.
9. A method of treating interleukin-1 mediated bone metabolism disorders in a mammal in need thereof which comprises administering to said mammal an interleukin-1 mediated bone metabolism disorder treating amount of a compound of the formula

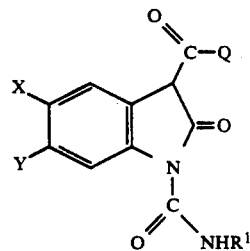

or a pharmaceutically-acceptable base salt thereof, wherein X and Y are each H, F, Cl, Br or CF$_3$; R$^1$ is H or (C$_1$–C$_4$) straight or branched-chain alkyl; and Q is

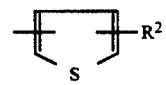

where R$^2$ is H or (C$_1$–C$_3$)alkyl, provided that when R$^2$ is H, R$^1$ is not H.

10. The method according to claim 9 wherein Q is

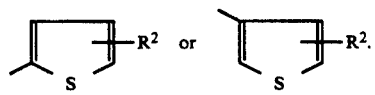

11. The method according to claim 9 wherein R$^1$ is t-butyl.
12. The method according to claim 9 wherein R$^1$ is H.
13. The method according to claim 10 wherein X is Cl; Y is H; R$^1$ is H, ethyl or t-butyl; and R$^2$ is H or CH$_3$.
14. The method according to claim 10 wherein X is Cl, Y is H, R$^1$ is H; and R$^2$ is CH$_3$.
15. The method according to claim 9 wherein the compound or a pharmaceutically-acceptable base salt thereof is administered orally.

16. The method according to claim 9 wherein the compound or a pharmaceutically-acceptable base salt thereof is administered parenterally.

17. The method according to claim 9 wherein the bone metabolism disorder is osteoporosis.

18. The method according to claim 13 wherein the bone metabolism disorder is osteoporosis.

19. The method according to claim 14 wherein the bone metabolism disorder is osteoporosis.

20. A method of treating interleukin-1 mediated connective tissue metabolism disorders in a mammal in need thereof which comprises administering to said mammal an interleukin-1 mediated connective tissue metabolism disorder treating amount of a compound of the formula

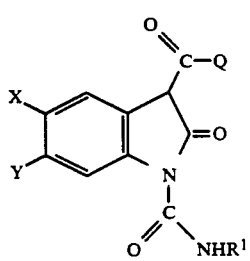

or a pharmaceutically-acceptable base salt thereof, wherein X and Y are each H, F, Cl, Br or $CF_3$; $R^1$ is H or $(C_1-C_4)$ straight or branched-chain alkyl; and Q is

where $R^2$ is H or $(C_1-C_3)$alkyl, provided that when $R^2$ is H, $R^1$ is not H.

21. The method according to claim 20 wherein Q is

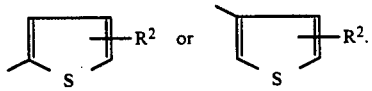

22. The method according to claim 20 wherein $R^1$ is ethyl or t-butyl.

23. The method according to claim 20 wherein $R^1$ is H.

24. The method according to claim 21 wherein X is Cl; Y is H; $R^1$ is H, ethyl or t-butyl; and $R^2$ is H or $CH_3$.

25. The method according to claim 21 wherein X is Cl; Y is H; $R^1$ is H; and $R^2$ is $CH_3$.

26. The method according to claim 20 wherein the compound or a pharmaceutically-acceptable base salt thereof is administered orally.

27. The method according to claim 20 wherein the compound or a pharmaceutically-acceptable base salt thereof is administered parenterally.

28. The method according to claim 20 wherein the connective tissue metabolism disorder is periodontal disease or tissue scarring.

29. The method according to claim 24 wherein the connective tissue metabolism disorder is periodontal disease or tissue scarring.

30. The method according to claim 25 wherein the connective tissue metabolism disorder is periodontal disease or tissue scarring.

31. A method of treating interleukin-1 mediated immune dysfunction in a mammal in need thereof which comprises administering to said mammal an interleukin-1 mediated immune dysfunction treating amount of a compound of the formula

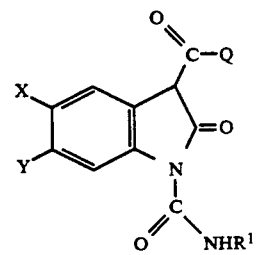

or a pharmaceutically-acceptable base salt thereof, wherein X and Y are each H, F, Cl, Br or $CF_3$; $R^1$ is H or $(C_1-C_4)$ straight or branched-chain alkyl; and Q is

where $R^2$ is H or $(C_1-C_3)$alkyl, provided that when $R^2$ is H, $R^1$ is not H.

32. The method according to claim 31 wherein Q is

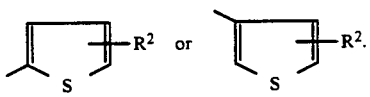

33. The method according to claim 31 wherein $R^1$ is ethyl or t-butyl.

34. The method according to claim 31 wherein $R^1$ is H.

35. The method according to claim 32 wherein X is Cl; Y is H; $R^1$ is H, ethyl or t-butyl; and $R^2$ is H or $CH_3$.

36. The method according to claim 32 wherein X is Cl; Y is H; $R^1$ is H; and $R^2$ is $CH_3$.

37. The method according to claim 31 wherein the compound or a pharmaceutically-acceptable base salt thereof is administered orally.

38. The method according to claim 31 wherein the compound or a pharmaceutically-acceptable base salt thereof is administered parenterally.

39. The method according to claim 31 wherein the immune dysfunction is allergy or psoriasis.

40. The method according to claim 35 wherein the immune dysfunction is allergy or psoriasis.

41. The method according to claim 36 wherein the immune dysfunction is allergy or psoriasis.

* * * * *

UNITED STATES PATENT AND TRADEMARK OFFICE
CERTIFICATE OF CORRECTION

PATENT NO. : 5,192,790

DATED : March 9, 1993

INVENTOR(S) : Carl J. Goddard et al.

It is certified that error appears in the above-identified patent and that said Letters Patent is hereby corrected as shown below:

At column 1, line 44, "$-(CH_2)_2-Q-R°$" should read -- $-(CH_2)_n-Q-R°$ --;

At column 8, line 31, "glutami" should read --glutamine--;

At column 8, line 53, "RPMI-SP$^4$" should read --RPMI-SF$^4$--;

At column 8, line 65, "in which" should read --in--; and

At column 9, line 67, "$(C_1-C_3)$ alkyl that" should read --$(C_1-C_3)$ alkyl, provided that--;

At column 8, line 62, "otherwise refrigerated or frozen" should read --otherwise refrigerated or frozen for subsequent assay.--.

Signed and Sealed this

Twenty-ninth Day of March, 1994

Attest:

BRUCE LEHMAN

*Attesting Officer*  *Commissioner of Patents and Trademarks*